United States Patent [19]
Hoff

[11] 3,935,860
[45] Feb. 3, 1976

[54] INTRAUTERINE DEVICE WITH RESTRICTOR FOR MAINTAINING DEVICE IN UTERINE CAVITY

[75] Inventor: Seymour Hoff, San Jose, Calif.

[73] Assignee: Alza Corporation, Palo Alto, Calif.

[22] Filed: Aug. 21, 1974

[21] Appl. No.: 499,185

[52] U.S. Cl. ............................ 128/130; 128/260
[51] Int. Cl.² ............................................. A61F 5/46
[58] Field of Search ....................... 128/127–131, 128/1 R, 341, 343, 260, 244, 345; 74/520, 521; 85/3 R, 3 S, 71, 80

[56] References Cited
UNITED STATES PATENTS

| | | | |
|---|---|---|---|
| 2,072,066 | 2/1957 | Cossentine | 85/3 R |
| 3,182,662 | 5/1965 | Shirodcar | 128/127 X |
| 3,253,590 | 5/1966 | Birnberg et al. | 128/127 X |
| 3,454,004 | 7/1969 | Leininger et al. | 128/130 |
| 3,533,406 | 10/1970 | Tatum | 128/130 |
| 3,633,574 | 1/1972 | Lerner | 128/130 |
| 3,722,037 | 3/1973 | Jaeger | 85/80 X |
| 3,820,535 | 6/1974 | Marco | 128/130 |

FOREIGN PATENTS OR APPLICATIONS

| | | | |
|---|---|---|---|
| 447,562 | 7/1927 | Germany | 128/127 |

*Primary Examiner*—Lawrence W. Trapp
*Attorney, Agent, or Firm*—Paul L. Sabatine; Thomas E. Ciotti; Edward L. Mandell

[57] ABSTRACT

Intrauterine device with restrictor for maintaining device in uterine cavity having a transverse member and a dependent member connected to the transverse member at a locus on the dependent member with a restrictor on the dependent member for keeping the shape of the device in a resting uterus or a contracting uterus; thereby substantially eliminating the incident of involuntary expulsion from the uterus.

7 Claims, 9 Drawing Figures

INTRAUTERINE DEVICE WITH RESTRICTOR FOR MAINTAINING DEVICE IN UTERINE CAVITY

BACKGROUND OF THE INVENTION

The present invention pertains to an improvement in contraception. More particularly, the invention relates to both a novel and useful intrauterine contraceptive device.

It is known in the prior art the presence of an intrauterine device in the uterus of a fertile female can exhibit a high degree of reliability for the inhibition of conception and pregnancy. Moreover, this phenomenon has been medically used for the intentional prevention of conception and pregnancy by inserting a sized and shaped device into the uterus. While some devices have gained wide usage because of their efficiency and low cost, the practical use for these devices for their intended purpose has been associated with serious disadvantages. One such device in commercial use is comprised of a transverse member perpendicular to a dependent member substantially defining a T-shaped device.

One major disadvantage associated with the T-shaped device is its unacceptably high rate of involuntary expulsion from a viable uterus. This expulsion is most frequently a normal daily occurrence. The expulsion is due to sequential changes in the uterine wall during several degrees of contraction, with the energy of muscle tension converted into pressure that exerts a downward and outward force on the device. This force pushes the device totally or partially from the uterus. In partial expulsion, the dependent member is pushed through the cervical os. The overall expulsion rate for this device often exceeds seven percent and unplanned, unwanted pregnancies are associated with its expulsion. Contraception, Vol. 7, No. 6, pages 477 to 489, 1973.

SUMMARY OF THE INVENTION

This invention primarily concerns an intrauterine device comprised of a transverse member and a dependent member. The dependent member is connected to the transverse member at an interconnecting point along the transverse member. The transverse member can be perpendicular to the dependent member, it can have a curved-linear configuration or it can be wedged-shaped. A means is fixed on the dependent member for restricting the directional movement of the transverse member. The means, or restrictor, permits the transverse member to be easily folded down and in against the dependent member, and it makes it difficult for the transverse member to fold up and away from the dependent member. The restrictor also permits easy insertion and positioning in the uterine cavity and it additionally severely prevents upward movement of the transverse member to substantially eliminate involuntary expulsion from the cavity. The invention makes available to the art for the first time an improved intrauterine device that overcomes the disadvantages associated with the prior art devices while unexpectedly exhibiting a high degree of reliability for the inhibition of conception and pregnancy. Simultaneously, the device of the invention unobviously reduces the occurrence of total and partial expulsion from a resting or a contracting uterus.

BRIEF DESCRIPTION OF THE DRAWINGS

In the drawings, which are not drawn to scale, but rather are set forth to illustrate various embodiments of the invention, the drawings are as follows.

In the drawings and specification, like parts in related Figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 1:
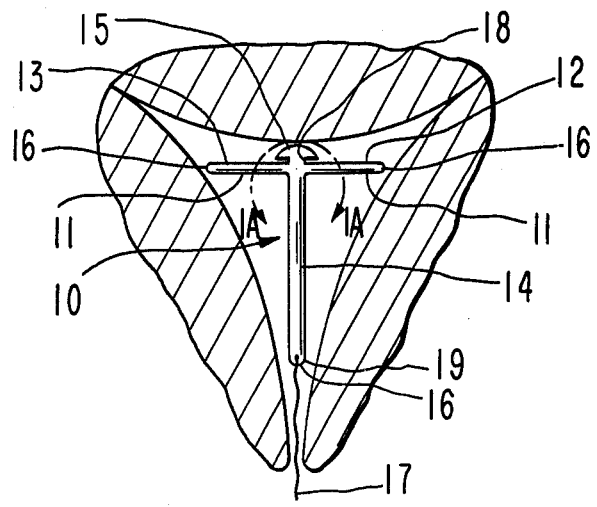
FIG. 1 is a front elevational fragmentary view showing an intrauterine device having a transverse member and a perpendicular dependent member with a means for controlling the directional movement of the transverse arms when positioned within a uterine cavity.

Turning now to the drawings in detail, which are examples of various improved intrauterine devices of the invention, and which examples are not to be construed as limiting, one embodiment of a novel device is indicated in FIG. 1 by the number 10. Intrauterine device 10 is comprised of a transverse member 11 suitably fixed to a dependent member 14. Member 14 has a lead end 18 and a distant end 19. Member 11 interconnects with member 14 at lead end 18 with member 11 projected outwards in two directions from member 11 to define arm 12 and arm 13, a right and left arm respectively, with upper and lower faces or surfaces. Arms 12 and 13 each terminate in an end 16 that is rounded to prevent any possible damage to the uterus, and it is sized and shaped to fit all cavities. Its dimensions conform to the nulliparous, parous and the multiparous cavities and it has a length of 20 to 40 mm. For farm animals, household pets, and sport animals, it is made to the appropriate size.

Member 14, when positioned in the cavity, is pointed up from member 11 towards fundus uteri and down towards the internal cervical os. A single string 17 is attached to member 14 at end 16 for manually removing device 10 from the uterus. Dependent member 14 is sized and shaped to fit nulliparous, parous and multiparous uterine cavities and it has a length of 20 to 40 mm.

Member 14, as does member 11, has a diameter of 1 to 4 mm.

Figure 1A:
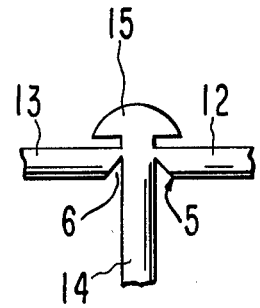

A restrictor 15 is positioned at the tip of dependent member 14 and extended over the fundal facing surface of transverse member 11 as a means for restricting or for preventing arms 12 and 13 from folding up and away from member 14. By preventing device 10 from assuming a linear-shaped configuration in the uterus with arms 12 and 13 pointed toward the fundus, restrictor 15 prevents involuntary expulsion of device 10. Contrawise, restrictor 15 lets flexible, resilient arms 12 and 13 fold down and in towards member 14 to define a linear-like shaped device for easy passage through the cervical os. Restrictor 15 is designed and shaped to extend over arms 12 and 13 a sufficient distance towards ends 16 on their fundus facing surface for making it hard for the arms to fold up. Restrictor 15 can be separately made and fixed on transverse member 11, it can be integrally formed as part of transverse member 11, and it is slightly raised above member 11, usually 0.0001 to 7.5 mm, or the like. Restrictor 15 has a uterine acceptable shape such as curvilinear, ball, rectangular with rounded corners, an enlargement of egg-shaped configuration, half-circle, crescent, ellipsoidal, oval, and the like. Modifications also can be made in device 10 for increasing the downward foldability of arms 12 and 13. For example, in FIG. 1A, transverse arms 12 and 13 have a means 6, that is a notch or indentation, at underside 5 as arms 12 and 13 extend from member 14. Means 6 insures unidirectional downward folding of arms 12 and 13 to make it easier for insertion and exceedingly hard for arms 12 and 13 to fold up from member 14.

Figure 2:
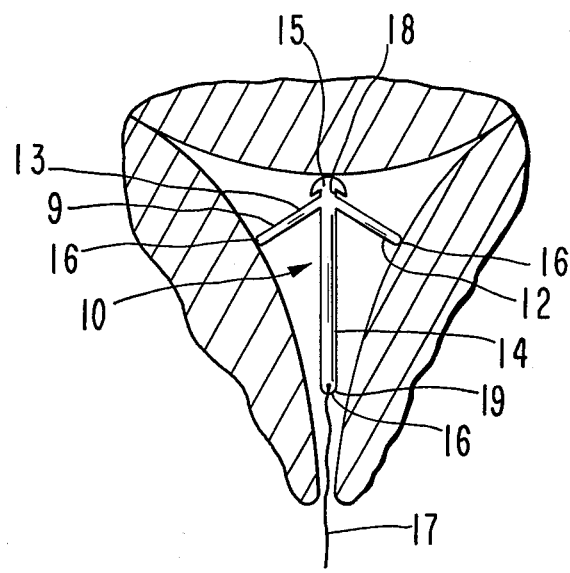
FIG. 2 is a partly diagrammatical front elevational view of an intrauterine device having a wedged-shaped transverse member and a dependent member within a uterine cavity.

In FIG. 2, there is depicted another device 10 prepared according to the spirit of the invention. The device of FIG. 2 possesses a specifically different configuration and advantages than the device of FIG. 1. Device 10 of FIG. 2 is comprised of a wedged-shaped member 9 fixed to a dependent member 14 to generally define an arrow. Member 9 and member 14 can connect anywhere along member 9 from within ends 16 to the mid-point of member 9. Wedged-shaped member 9 has two arms, 12 and 13, which project slightly downward from member 14 in a coplanar nonperpendicular arrangement. Arms 12 and 13 terminate at rounded end 16. Member 14 has a lead end 18 and a distant end 19 with end 19 having a string 17 attached at its rounded end 16. A restrictor 15, which is either fixed or integrally formed, is positioned at lead end 18 for controlling the directional movement of arms 12 and 13 in a single direction, mainly down. Restrictor 15 is larger than dependent member 14 and it has the definite advantage of substantially eliminating expulsion. Its inside diameter is larger than the inside diameter of member 14 and these structural features additionally enhance insertion of the device. Device 10 can be fabricated into many sizes, shapes and thicknesses for adaptation to different uteri. Device 10 is structured to perform in situ as previously described in FIG. 1 to maintain device 10 in the uterus during resting periods and contraction periods.

Figure 3:
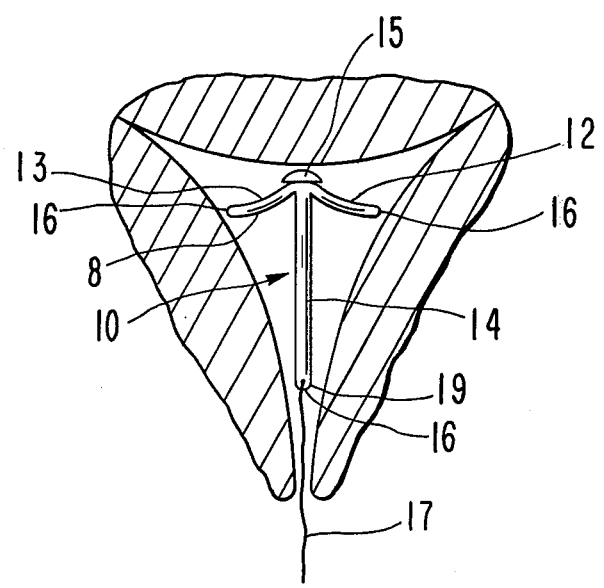
FIG. 3 is a frontal view of another intrauterine contraceptive device of the invention depicting a curved-linear transverse member fixed to a dependent member with a moderator for restricting movement of the curved member in a single direction placed in an intrauterine cavity.

In FIG. 3, there is provided a device 10 comprised of a filamentary body formed of a curved strand 8 connected to an elongated straight member 14. Strand 8 is formed with a pair of arms 12 and 13, with each arm terminated in rounded marginal ends 16. Strand 8 is curved to readily adapt to the curved configuration of the fundus, and it provides the necessary endometrial surface coverage for contraceptive effectiveness. Member 14 interconnects with strand 8 at any point along strand 8 from end 16 to the mid-point and it terminates in a rounded end 16. A string 17 is tied to end 16. A unidirectional guidance member 15 is attached to the side opposite the connecting point of strand 8 and member 14 at the corresponding point on strand 8. Member 15 is larger than member 14 for enhancing insertion and in the uterus, it prevents arms 12 and 13 from moving up and away from member 14. Device 10 can be designed, sized and shaped to conform to a specific uterine cavity, yet a wide variance in sizes can be made with guidance member 15 maintaining the device in the uterus during prolonged periods of time.

Figure 4:
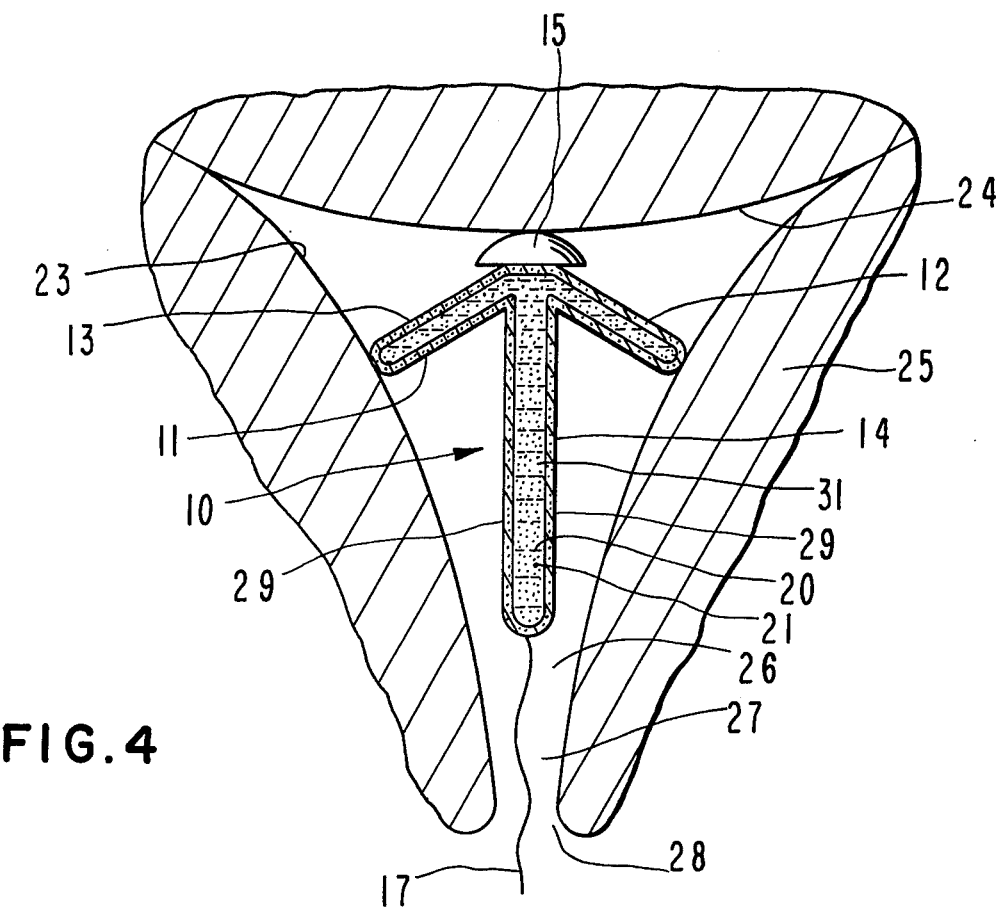
FIG. 4 is an enlarged frontal fragmentary view of another embodiment of the invention illustrating a contraceptive agent-releasing device within a fertile uterus.

FIG. 4 illustrates another device 10 of the invention. Device 10 structurally encompases most of the structure of device 10 of FIG. 1 with a few differences; mainly, means 15 is rectangular shaped with rounded corners and a contraceptive agent 35 is wrapped on a transverse arm and on the dependent member. If preferred, either a single arm or the entire device can be wrapped with agent 35. Agent 35 is a wire made of a member selected from the group consisting of copper and zinc and mixtures thereof. These metals and alloys also can be applied on the device by coating, encasing the arms in a metal sleeve, or the like. The use of copper and zinc as a contraceptive agent is disclosed in U.S. Pat. No. 3,563,235. The amount of agent 35 on device 10's exposed surface is about 25 to 400 mm$^2$, for releasing a contraceptively effective amount of copper ion, zinc ion or a mixture thereof when placed in a fertile uterine cavity of an adult woman.

Figure 5:
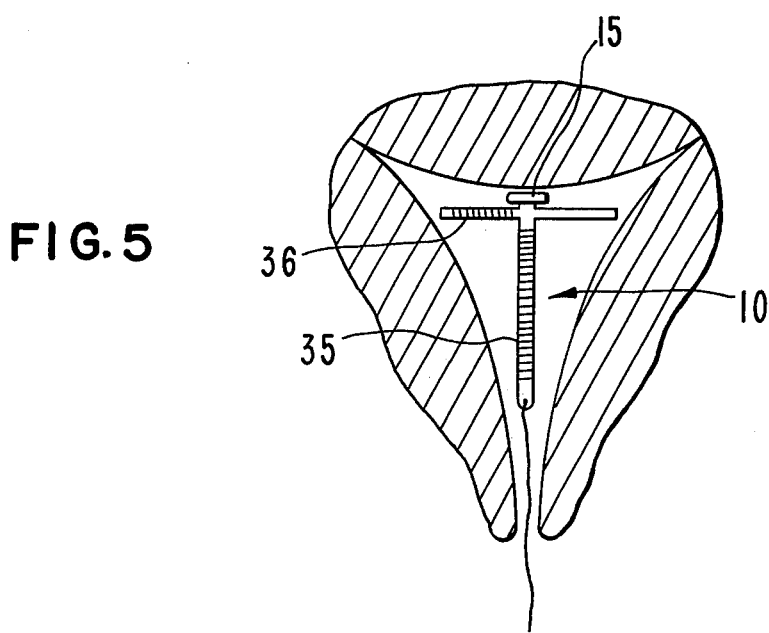
FIG. 5 illustrates another embodiment of the invention by showing a device releasing a contraceptively effective amount of a metal ion within the uterus of a mature, adult, child-bearing woman.

In FIG. 5, there is graphically illustrated another device 10 prepared according to the mode and manner of the invention. Device 10 of FIG. 5 is comprised of a transverse member 11 having arms 12 and 13, and a dependent member 14. A string 17 is fixed to the trailing end of member 17. A means 15 for maintaining the predesigned structural shape of device 10 is formed on the lead-end of member 14. Device 10 is comprised of a wall 29 surrounding a reservoir 31 containing a carrier 20. Carrier 20 contains antifertility agent 21. Device 10 is designed and adapted to be located within uterine cavity 25. Device 10 contacts the sides 23, as well as fundus uteri 24, of uterus 25. Device 10 is placed in uterus 25 through external cervical os 28, cervical canal 27 and internal cervical os 26.

Carrier 20 contains antifertility agent 21 or a mixture of antifertility agents, and it is permeable to the passage of agent 21, but the rate of passage of agent 21 through wall 29 is lower than the rate of passage of antifertility agent through carrier 20. In operation, carrier 20 serves as a reservoir 31 by supplying dissolved antifertility agent 21 to wall 29 as molecules move through the carrier to bathe the inner surface of wall 29. Antifertility agent 21, present at the antifertility carrier/wall interface, dissolves in and migrates through wall 11, ultimately reaching the outer surface of wall 29 for release in the uterine cavity. As antifertility agent 21 leaves carrier 20, undissolved agent 21 present in reservoir 31, dissolves in carrier 17 to maintain a constant supply of dissolved antifertility agent in carrier 20 for continuously supplying it at substantially the same rate to wall 29. Wall 29 operates to effectively control the rate of release of antifertility agent throughout the useful period of birth control by the device. Thus, a zero order antifertility release rate can be obtained.

Wall 29 of device 10 can be made of substantially imperforate homogenous material that releases agent 21 by diffusion, or wall 29 can be made of a microporous material that releases agent 21 by diffusion through a media in the micropores of wall 29. When wall 29 releases agent 21 by diffusion, the agent dissolves and equilibriates in wall surface, and then diffuses in the direction of lower chemical potential. At the second boundary equilibrium is again established. When the boundary conditions on both sides of the wall are maintained constant, a steady flux of the agent will be established which can be described by Fick's Law of Diffusion. The rate of passage of the agent through the wall material is dependent on the solubility of the agent, as well as on the thickness of the material. This means that selection of appropriate materials for fabricating the wall will be dependent on the particular agent to be used. By varying the composition and thickness of wall 29, the dosage rates per area of the device can be controlled, for this material acts to meter the diffusion of the agent from the reservoir. In reservoir devices of this invention, the materials comprising wall 29 are chemically and/or structurally different than the material comprising carrier 20 of reservoir 31. Carrier 20 of reservoir 31 is permeable to the passage of agent, but the rate of diffusion or passage through wall 29 is lower than the rate of diffusion or passage through carrier 20, so that the rate of passage of the agent through wall 29 is the rate release controlling step for the device. Thus, through this invention, as described in FIG. 5, devices of the same surface area, functioning by diffusion, can give different dosages of agent 21 by varying the characteristics of wall 29 to give controlled administration of agent 21.

In the devices of the invention as set forth in FIG. 5, when wall 29 is formed from a release rate controlling microporous material that is permeable to agent 21, agent 21 transfer mechanism is by diffusion through a medium contained in the micropores of the material at a controlled and predetermined rate. That is, in this material, the rate of passage or the rate of agent release through wall 29 is governed by diffusion of tthe agent through a diffusive medium present in the pores, microholes and cracks of the material forming the wall. The diffusive medium, in one embodiment, is a liquid phase comprised of a colloidal solution having excess agent 21, a suspension containing excess agent 21, or a sol containing excess agent 21, and the carrier can be polar, semi-polar or non-polar. In these diffusive media, the agent can have different degrees of solubility, such as fully soluble, partially soluble and the like, to act in cooperation with the material for achieving a controlled release rate. Carrier 20 also has a high diffusivity for antifertility agent 21.

The diffusive medium can be added to the microporous material by methods well known to the art, for example, by immersion of the material in a bath containing the medium to let the medium partially fill or fully saturate the micropores of the material. Another method for charging the micropores with a diffusive medium is to first add to the reservoir a diffusive medium, or a mixture of diffusive media so that the medium can flow from within the reservoir into the pores and remain therein to permit diffusion of later added agent, but not its solubilizing limited carrier, to pass therethrough. The media suitable for the immersion purpose are those well known to the art such as water, glycerin, ethylene glycol, propylene glycol, castor oil, olive oil, alcohols of 2 to 10 carbon atoms, halogenated hydrocarbons having 2 to 20 carbon atoms, aldehydes, and ketones having 4 to 10 carbon atoms, syrups, and the like. Additionally, the medium can be emulsifying and suspending agents such as methyl cellulose mixed with water, mixtures of propylene glycol monostearate and oils, gum tragacanth and water, assorted waxes and the like. Representative mediums are set forth in *Remington's Pharmaceutical Science*, pages 246 to 269 and 1338 to 1380, 1970, published by Mack Publishing Company, Easton, Pa.

In another embodiment, the medium can be added to the pores and cracks of the material forming wall 29 by locating wall 29 in a fluid environment, for example, by contacting the device with a body tissue, for example, the mucous membranes of the uterus, that can make available its intracellular and/or extracellular fluid for subsequent transfer into the micropores of wall 29 for functioning as a medium for the drug. In another embodiment, the pores can be filled with plasticizer by immersing wall 29 in a plasticizer solvent composition, and removing the solvent in vacuo after the filling of the pores. Exemplary plasticizers suitable for employment of the present purpose are the commercially available plasticizers conventionally used for the manufacture of polymeric materials such as diethyl adipate, di-isobutyl adipate, di-n-hexyl adipate, di-iso-octyl adipate, di-n-hexyl azelate, di-2-ethylhexylazelate, ethylene glycol dibenzoate, acetyl tri-n-butyl citrate, epoxidized soy bean oil glycerol monoacetate, diethylene glycol dipelargonate, propylene glycol diluarate, isooctyl palmitate, triphenyl phosphate, and the like.

The materials comprising wall 29 are chemically and/or structurally different than the materials comprising carrier 20. Both of the materials are permeable to the passage of antifertility agent 21, but the rate of flow through wall 29 is lower than the rate through carrier 20. Thus, the rate of passage of the agent through wall 29 is the rate release controlling step for the device. Generally, for the practice of this invention, the ratio of the agent release rate through carrier 20 of reservoir 31 to the agent release rate through wall 29 should be from 100:1 to 2:1 and preferably from 10:1 to 2:1. Of course, the invention is not limited to these release rates as the invention comprises lower or higher release rates from carrier 20 and lower and higher rates through wall 29 with the release rate of wall 29 lower than the release rate of carrier 20. Thus, the invention provides that devices of the same surface area, activated by diffusion, can give different dosages of a drug by varying the characteristics of the wall material to give controlled administration of an antifertility agent; *Encyclopedia of Polymer Science and Technology*, Vol. 9, pages 794 to 807, 1968.

For either of the above discussed mechanisms, diffusion through a homogenous material, or diffusion through a medium present in the micropores and cracks of a material, the transfer or rate of release of antifertility agent 21 through wall 29 is at a lower rate than the rate of release of agent 21 from carrier 20 of reservoir 31 for administration to the receptor site. Thus, the passage of agent 21 through wall 29 is the release rate controlling step for the agent delivery system. In addition, because reservoir 31 serves to transfer antifertility molecules 21 to all areas of wall 29, wall 29 of the delivery device housing the reservoir remains substantially at the thermodynamic activity corresponding to that of agent 21 until substantially all of agent 21 has been released from reservoir 31. Ordinarily, one would expect migration of antifiertility agent 21 from the reservoir 31 to cease when sufficient agent 21 has entered wall 29 to establish an equilibrium; however, when the delivery device is in situ, molecules are continuously removed from the outer surface of the wall. For optimum results, the rate of release of agent 21 through wall 29 should be less than the rate of clearance of migrated agent 21 from the external surface of device 10. This ensures that agent 21 administration rate is dependent on the rate of release of agent 21 through wall 29 which can be controlled by device 10, rather than upon clearance of agent 21 from device 10 in vivo, which can vary. Thus, in contrast to previously proposed intrauterine contraceptive delivery devices, the rate of release of agent 21 from device 10 of the invention can remain essentially constant until the intrauterine contraceptive device 10 has substantially completed its useful function.

The term "reservoir" 31 as used in the specification, and the accompanying claims, generally refers to a "carrier" or to a "medium containing the antifertility agent," that constantly bathes the innver surface of the release rate controlling wall and supplies agent thereto. That is, the reservoir is comprised of a carrier material containing dissolved agent, and/or excess undissolved agent, and/or a mixture of both, and it is a material that is permeable to the passage of agent 21 as by diffusion or convection. The carrier medium used for the purpose of the invention is a solid or a liquid, and it can be inorganic or organic, and of naturally occurring or synthetic origin. Examples of carriers comprised within the term are, for example, immiscible liquids containing excess undissolved agent, emulsions, gels, sols, jellies, colloids, oils, syrups, suspensions, dispersions, liquid pre-cured polymers, liquid polymers, liquid plasticizers, liquid thixotropic agents, polar solvents, semipolar solvents, nonpolar solvents, liquid-like mediums, mixtures thereof, and the like. These carriers contain excess undissolved replacement agent 21 for replenishing released agent 21.

The carrier comprising the reservoir also has, in addition to the properties described supra, limited solubility for the contained antifertility agent or for a mixture of agents. By limited solubility is meant that the agent is soluble in given amounts in the carrier, that is, it comprises varying concentrations of the agent dissolved in the carrier. Essentially, there is also an excess amount of undissolved agent present in the carrier that acts as replacement agent to replace agent released from the device, thereby maintaining a saturated concentration of the agent in the reservoir throughout the dispensing life of the device. Generally, the amount of undissolved agent initially present in the reservoir will range from about 90 percent by weight to about 99.9 percent by weight of the total amount of agent present in the reservoir. By limited solubility as used herein, is meant solubility concentrations include solubilities such as, soluble, sparingly soluble, slightly soluble, very slightly soluble, and almost practically insoluble. Generally, on a weight basis at 25°C, the amount of the agent dissolved in a carrier that is termed a soluble carrier is about 1 part of agent to about 10 to 25 parts of carrier, the amount of agent dissolved in a carrier that is sparingly soluble for the agent is 1 part of agent to about 25 to 100 parts of carrier, from 100 to 1000 parts of carrier for 1 part of agent when the agent is very slightly soluble in the carrier, and from 10,000 to 15,000 parts of carrier for 1 part of agent in a carrier that is almost practically insoluble for the drug. Hence, the term limited solubility comprises a range of solubility of the agent in a carrier of 1 part of agent to about 10 to 15,000 parts of carrier on a weight basis at 25°C. The above ranges are set forth to aid in defining the invention, and they should not be considered as limiting as other ranges at higher or lower temperatures are embraced within the above presentation are also included herein.

The materials suitable for fabricating wall 29 of the intrauterine device 10 are generally those materials capable of forming wall 29, with or without micropores, through which the agent can pass at a controlled rate of release by diffusion. Such materials are referred to in this specification and the appended claims as "release rate controlling materials." Suitable materials for forming the wall are naturally occurring or synthetic materials preferably materials that are biologically compatible with body fluids, and uterine tissues, and essentially insoluble in body fluids found in the vagina and cervix, with which device 10 will come in contact.

Exemplary naturally occurring or synthetic materials suitable for fabricating the wall are release rate controlling materials such as natural rubber, poly(isoprene), poly(isobutylene), poly(butadiene), poly(ethylene), plasticized poly(vinylidene chloride), cross-linked poly(vinylpyrrolidone), and the like. Also, by way of non-limiting example, copolymers such as non-toxic vinylchloride diethyl fumarate, and the like. Examples of other materials include silicone rubbers, especially the medical grade poly(dimethylsiloxanes), and siliconcarbonate copolymers; modified insoluble collagen, cross-linked insoluble poly(vinylalcohol), cross-linked partially hydrolyzed insoluble poly(vinylacetate), and surface treated silicone rubbers as described in U.S. Pat. No. 3,350,216. Other polymeric membranes that are biologically compatible and do not adversely affect the drugs can be used.

Additionally, other materials permeable to the passage of the antifertility agent that are suitable for the present purpose include copolymers such as oxide, poly(vinylbutyral) comprised of 11 to 45 percent free hydroxyls, anisotropic permeable microporous membranes of ionically associated polyelectrolytes, the microporous polymers formed by the coprecipitation of a polycation and a polyanion as described in U.S. Pat. Nos. 3,276,589; 3,541,005; 3,541,006; 3,546,142; and the like; treated aliphatic polyamide membranes as in U.S. Pat. Nos. 2,071,253; 2,966,700; 2,999,296; and the like; plasticized vinylidene cloride vinyl chloride copolymer 40/60 and 10/90; water insoluble natural gums, and the like. Also, materials such as regenerated cellulose diacetate, cellulose triacetate poly(urethane), and the like. Materials having a pore size of several hundred microns or larger, or down to several angstoms or smaller. For example, the wall can comprise regenerated insoluble, nonerodible cellulose, poly(electrolytes) with a pore size of 7 to 50A, epoxy resins, poly(olefins), plasticized poly(vinylchlorides) with a pore size of about 50A or less to 150 microns or larger as conventionally made by leaching out incorporated salts, soap micelles, starch or the like materials to give a microporous membrane. Also, the materials that can be used include those materials having homogenous properties and microporous properties, such as cross-linked gelatinous membranes, and the like.

The carrier 20 used to form the reservoir 31 containing the antifertility agent 21 is comprised of materials of naturally occurring or synthetic origin, of the inorganic or organic types that do not adversely affect the agent, or the mixture of agents contained therein, and which are permeable to the passage of the agent. Generally, the carrier used is a solid or a liquid that does not leave or diffuse from the reservoir. Examples of carriers include gelatin, alginates, agar-agar, ethylcellulose, ethylene glycol, ethylene glycol monomethyl ether, polyethylene glycols having a molecular weight of 200 to 600, methyl isobutyrate, corn oil, castor oil, olive oil, liquid prepolymers, emulsions of gum arabic, silicon oil, sodium carboxymethylcellulose, and the like. The carrier also can contain suitable dispensing agents such as lecithin, polyoxyethylene stearate, and the like; carriers such as acetamide, N,N-dimethyl acetamide, N-(2-hydroxyethyl) acetamide, and the like. Additionally, the carrier can contain adjuvants such as preserving, stabilizing, or wetting agents, and the like.

The rate of release of an agent through various release rate controlling materials can easily be determined by those skilled in the art by standard procedures. In this manner, particular materials used as the device wall as the agent release rate controlling barrier for release of drug from the reservoirs can be selected. Various techniques, such as the transmission method, the sorption-desorption method and the like, can be used as measurers of permeability. One technique that has been found to be eminently well suited is to cast or hot press a film of the material to a thickness in the range of 2 to 60 mils. The film is used as a barrier between a rapidly stirred (e.g., 150 r.p.m.) saturated solution of the drug and a rapidly stirred solvent bath, both maintained at constant temperature (typically 37°C). Samples are periodically withdrawn from the solvent bath and analyzed for agent concentration. By plotting the agent's concentration in the solvent bath versus time, the permeability coefficient P of the material is determined by Fick's First Law of Diffusion.

$$\text{Slope of plot} = \frac{Q_1 - Q_2}{t_1 - t_2} = P \frac{AC}{h}$$

Wherein
- $Q_1$ = cumulative amount of drug in solvent in micrograms at $t_1$
- $Q_2$ = cumulative amount of drug in solvent in micrograms at $t_2$
- $t_1$ = elapsed time to first sample, i.e. $Q_1$
- $t_2$ = elapsed time to second sample, i.e. $Q_2$
- A = area of membrane in $cm^2$
- C = initial concentration of drug
- h = thickness of membrane in $cm^2$ By determining the slope of the plot, i.e.

$$\frac{Q_1 - Q_2}{t_1 - t_2}$$

and solving the equation using the known or measured values of A, C, and h, the permeability P constant in $cm^2$/time of the material for a given agent is readily determined.

Using the above technique, the permeability coefficient P of the antifertility agent progesterone from isotonic solution through different materials into isotonic solution at 37°C was found to be:

| Membrane | Permeability Coefficient ($cm^2$/hr) |
|---|---|
| Poly(dimethylsiloxane) | $8.0 \times 10^{-2}$ |
| Poly(ethylene) | $4.7 \times 10^{-4}$ |
| Ethylene vinyl acetate copolymer- 9% vinyl acetate | $3.8 \times 10^{-3}$ |
| Silicone-polycarbonate copolymer- General Electric MEM 213 | $12.6 \times 10^{-3}$ |

By using the above technique to design a device for to releasing progesterone, one would employ poly(ethylene) as the material for the wall if a slow rate of release is desired, and poly(dimethylsiloxane) membrane for the wall if a faster rate of release is desired. If a faster rate of release than the rate of release through poly(ethylene) but slower than the rate of release than through poly(dimethylsiloxane) is preferred for progesterone, the copolymer ethylene vinyl acetate or silicone polycarbonate copolymer can be used as material. The use of ethylene vinyl acetate copolymer for devices as a drug release rate controlling material is the invention of Higuchi and Hussain as disclosed and claimed in U.S. Pat. application No. 281,446, filed on Aug. 17, 1972. Poly(ethylene), poly(dimethylsiloxane), ethylene vinyl acetate copolymer and silicone-polycarbonate copolymer are commercially available polymers. The poly(dimethylsiloxane) is available as Silastic 340 from Dow Corning Co. The poly(ethylene) is a low density polymer with a melt index of 0.85. These examples can be used to determine the rate of release through materials by techniques known to the art as in J. Pharm. Sci., Vol. 52, pages 1145 to 1149, 1963; ibid., Vol. 53, pages 798 to 802, 1964; ibid., Vol. 54, pages 1459 to 1464, 1965; ibid., Vol. 55, pages 840 to 843 and 1224 to 1239, 1966; Encyl. Polymer Sci. Technol., Vol. 5 and 9, pages 65 to 82 and 794 to 807, 1968; the references cited therein, and the like.

The rate of solubilization, or the rate at which the antifertility agent will go into solution is quantitatively governed by physico-chemical principles. For an example, a particle of an agent dispersed in a solvent is surrounded by a thin layer of solvent having a finite thickness $l$ in cm. This layer is considered as an integral part of the agent and it is characteristically referred to as the "stagnant layer." The stagnant layer remains a part of the surface of the agent, moving wherever the agent moves. Using Fick's First Law of Diffusion, the rate of solution is the rate at which a dissolved agent diffuses through the stagnant layer for supplying agent ot the reservoir's inner wall. The driving force behind the movement of the agent through the stagnant layer is the difference in concentration of the agent, $C_1$, in the stagnant layer at the surface of the agent and the concentration $C_2$ on the farthest side of the stagnant layer. The difference in concentation $C_1 - C_2$ determines the rate at which agent is solubilized in the carrier. Hence, if the carrier on the farthest side contains its optimum concentration because of a low release by the agent release rate controlling wall, the rate of solubilization of new agent will be low. Correspondingly, as agent leaves the carrier, new agent is solubilized to establish a steady state within the carrier.

The rate of diffusion of the antifertility agent in a solubilizing limiting carrier is broadly determined by measuring the rate an agent transfers from one chamber through a sintered glass filter of known pore size and thickness into another chamber at atmospheric pressure and room temperature about 25°C, or body temperature 37.5°C, and calculating from the obtained data the agent's transfer rate. The method is carried out by adding to a first conical flask equipped with a ground glass stopper and a stirring bar, a measured amount of carrier and simultaneously, the agent in the same carrier is added to a second conical flask similarly equipped while keeping the level of the carrier in the two flasks the same. Next, the flasks are stirred, and samples drawn at various time intervals for analysis. The measured rate of agent transport through the sintered glass filter, and the concentration difference of the agent in the two flasks is then calculated. These procedures are known to the art in *Proc. Roy. Sci. London*, Ser. A, Vol. 148, page 1935; *J. Pharm. Sci.*, Vol. 55, pages 1224 to 1229, 1966; and references cited therein. The diffusion coefficient of an agent can also be experimentally determined by using the above apparatus and references, or similar apparatus and procedures as described in *Diffusion in Solids, Liquids and Gases*, by W. Jost, Chapter XI, pages 436 to 488, 1960, Revised Edition, Academic Press, Inc., New York.

Also, according to Fick's Law, the rate of an agent's solution is directly proportional to the area of the agent, A in cm$^2$, as exposed to carrier and inversely proportional to the length of the path through which the dissolved agent molecule must diffuse. Then, the rate of solution of the agent is gen by $R = DA/l (C_1 - C_2)$ wherein R is the rate of solution, D is a proportionality constant called diffusion coefficient in cm$^2$/sec, and $C_1$, $C_2$ and $l$ are as previously defined. See *Remington Pharmaceutical Science*, 14th Ed., pages 246 to 269, 1970, Mack Publishing Company.

The solubility of the antifertility agent in the release rate controlling material comprising the wall of a device broadly is determined by preparing a saturated solution of a given antifertility agent and ascertaining, by analysis, the amount present in a definite area of the material. For example, the solubility of the agent in the wall is determined by first equilibrating the wall material with a measured saturated solution of the agent at a known temperature and pressure, for example 37°C and one atmosphere.

Next, agent is desorbed from the saturated wall material with a suitable solvent for the agent. The resultant solution for the agent then is analyzed by standard techniques such as ultraviolet, visible spectrophotometry, refractive index, polarography, electrical conductivity and the like, and calculating from the data the concentration, or solubility of the agent in the material.

The solubility of an agent in a liquid core can be determined by various art known techniques. One method consists in preparing a solution, for example, a carrier plus agent and ascertaining by analysis the amount of agent present in a definite quantity of the carrier. A simple apparatus for this purpsoe consists of a test tube of medium size fastened upright in a water bath maintained at constant temperature and pressure, for example 37.5°C and one atmosphere. The carrier and agent are placed in the tube and stirred by means of a motor driven rotating glass spiral. After a given period of stirring, a definite weight of the carrier is analyzed and the stirring continued for an additional period of time. If the analysis shows no increase of dissolved substance after the second period of stirring, the results are taken as the degree of solubility of the agent in the carrier. Numerous other methods are available for the determination of the degree of solubility of an agent in a liquid carrier. Typical methods used for the measurement of solubility are chemical analysis, measurement of density, refractive index, electrical conductivity, and the like. Details of various methods for determining solubilities are described in *United States Public Health Service Bulletin* No. 67 of the Hygienic Laboratory; *Encyclopedia of Science and Technology*, Vol. 12, pages 542 to 556, 1971, McGraw-Hill, INc.; *Encyclopaedic Dictionary of Physics*, Vol. 6, pages 545 to 557, 1962, Pergamon Press, Inc.; and the like.

In the specification and the accompanying claims, the phrase "anti-fertility agent," "contraceptive agent" and the term "agent" are used interchangeably and they broadly include progestational and estrogenic substances that have antifertility properties. The term "progestational substance" as used herein embraces "progestogen" which term is used in the steroid art to generically describe steroids possessing progestational activity, and the former also includes "progestins" a term widely used for synthetic steroids that have progesteroid effects. The active antifertility progestin or estrogenic agent that can be used to produce the desired effects in mammals, including humans and primates, include without limitation: progestational and estrogenic steroids such as the following: pregn-4-ene-3,20-dione; 19-nor-pregn-4-ene-3,20-dione; 17-hydroxy-19-nor-17α-pregn-5(10)-ene-20-yn-3-one; di-11β-ethyl-17-ethinyl-17-β-hydroxygn-4-ene-3-one; 17α-ethinyl-17-hydroxy-5(10)-estrene-3-one; 17α-ethinyl-19-norestosterone; 6-chloro-17-hydroxypregna-4,6-diene-3,20-dione; 17β-hydroxy-6α-methyl-17-(1-propynyl)-androst-4-ene- 3-one; 9β,10α-pregna-4,6-diene-3,20-dione; 17-hydroxy-17α-pregn-4-en-20-yne-3-one; 19-nor-17α-pregn-4-en-20-yne-3β,17-dial; 17-hydroxypregn-4-ene-3,20-diene; 17-hydroxy-6α-methylpregn-4-ene-3,20-dione; estratroil, estrone, 17β-estradoil, ethynyl estradoil, mixtures thereof, and the like.

Additionally, the above progestational and estrogenic agents in the form of their pharmacologically accepted derivatives, such as, their hydroxy or keto groups can be used for the present purpose. The progestational or estrogenic derivative used should easily convert to the parent agent upon its release from the device by biological activities such as enzymatic transformation, pH assisted hydrolysis in uteri, and the like. The derivative can also be used to control the solubility of the agent in the solid or liquid core and to assist in metering the agent from the device. Suitable derivatives include without limitation, esters with pharmaceutically acceptable acids such as acetate, glucuronate, benzoate, propionate, butyrate, valeroate, hexanoate, heptanoate, maleate, citrate, succinate, tartrate, fumerate, malate, ascorbate, sulphate, phosphate and the like.

The amount of agent present in the reservoir, whether dissolved, partially dissolved or undissolved is generally non-limited and it is an amount equal to or larger than the amount of an agent that on its release from the device is effective for being about the agent's antifertility effect. For example, the amount of agent present in the reservoir of an intrauterine device when the device is used for a predetermined period of time to achieve an antifertility effect in a potential childbearing woman is for pregn-4-ene-3,20-dione for a year supply wherein a year is 400 days, and the rate of release from the device is 25 micrograms per day is 10 mg in the reservoir, at the same rate of release for 2 years, a reservoir supply of 20 mg and for 3 years, 20 mg. If the rate of release for the same progestational agent is 100 micrograms per day and the length of the year is as before, the reservoir concentration of 1 year is 40 mg, for 2 years 80 mg and for 3 years, 120 mg. The amount of progestational agent present in the reservoir for a 1 year, 2 year and 3 year device is 80 mg, 160 mg and 240 mg respectively when the rate of release is 200 micrograms per day. Of course, for shorter periods or longer periods smaller amounts or larger amounts will be present in the reservoir, and the amount will also vary relative to the degree of activity of the progestational agent. Generally, the intrauterine contraceptive device will contain from about 0.1 mg ot 10 g of a progestational or estrogenic agent for releasing it at a controlled rate of from about 5 micrograms to 300 mirograms of agent, or larger amounts per day to a fertile uterus of an adult woman weighing 75 to 200 pounds. Of course, devices containing different amounts of agent for use for different time periods such as week, month, and the like, are also readily made by the invention.

An intrauterine antifertility dispensing device 10 comprises of a transverse curved member and an interconnecting dependent member with a means for maintaining the device in the uterus during resting pressure and contraction and having a reservoir comprised of a liquid core containing an antifertility agent and permeable to the passage of the agent is surrounded by a wall of an antifertility release rate controlling material permeable to the agent is manufactured as follows: first, a reservoir comprised of a liquid core consisting of 11 percent by weight of progesterone and 10 percent by weight of barium sulfate in a mixture of 3 parts by weight of Dow-Corning Silastic 382 elastomer resin liquid silicone oil and 1 part by weight of Dow-Corning 360 medical grade fluid silicone oil are thoroughly mixed in a standard laboratory v-blender to yield a liquid core. The progesterone is sparingly soluble in the liquid core. Next, an aliquot of the liquid core is injected into a section of medical grade polyethylene tubing having an outside diameter of 0.110 inches and an inside diameter of 0.070 inches and the ends of the tubing heat sealed with a standard, hand-held heater. The filled polyethylene tubing, about 6 cm in length, then is placed into the lower half of a two piece mold integrally shaped as a curved transverse member with a dependent member and a means disposed on the end of dependent member and extended along the curved transverse member. The upper half is placed thereon, and the upper half placed thereon. The mold is electrically heated to yield the shaped antifertility releasing device. The device will release about 25 to 30 micrograms of progesterone per day for controlling fertility in an adult woman.

Figure 6:
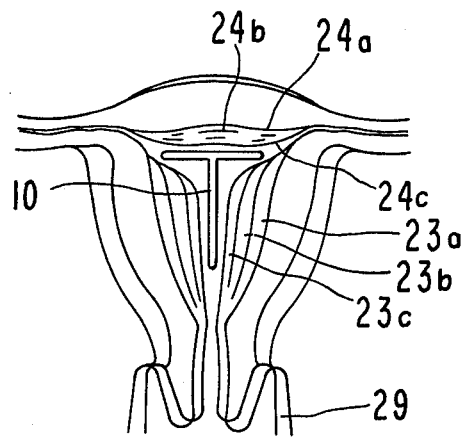
FIG. 6 is a schematic view of a contracting uterus expelling an intrauterine device.
Figure 7:
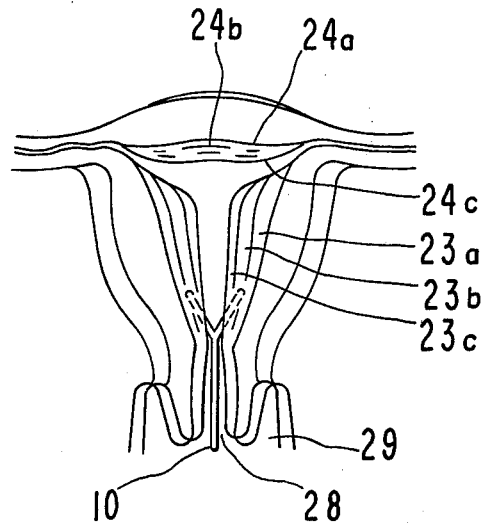
FIG. 7 is a schematic view illustrating a partially expelled device from a contracting uterus.
Figure 8:
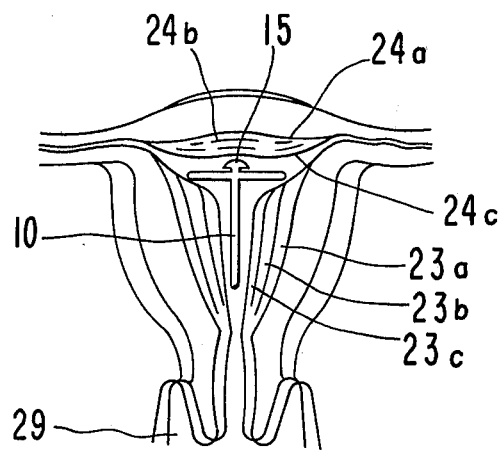
FIG. 8 is a frontal view depicting a device made according to the invention, resisting expulsion by a contracting uterus.

Expulsion has been one of the major concerns associated with the use of intrauterine contraceptive devices. This happens when the uterus, which is normally a cavity almost devoid of volume, has its volume increased by an intrauterine device and seeks to expell the device in an attempt to return to its normal volume. The uterus expells, or pushes the device from the uterus by undergoing sequential changes in the uterine walls and its cavity during several degrees of contraction from its increased volume down to its normal volume. Accompanying FIG. 6 shows in diagrammatic form sequential changes taking place in a uterus as it pushes a T-shaped device made according to U.S. Pat. No. 3,533,406 from a uterus. In FIG. 6, top uterine muscle 24a is seen moving through contractions 24b and 24c to exert a downward pressure on the device 10. Similarly, side uterine muscle 23a is seen moving through contractions 23b and 23c to apply additional pressure, lateral in this instance, on device 10. FIG. 7 shows the results of the contractions illustrated in FIG. 6 on device 10. In FIG. 7, device 10 is seen with its arms displaced and folded up to give device 10 an essentially linear configuration thereby making it easy for the uterus to involuntarily expell the device. FIG. 7 also shows device 10 almost pushed from the uterus into the vagina in an unwanted and useless position. As seen, the internal pressures applied on device 10 in the above manner leads to involuntary expulsion of intrauterine devices. In contrast to the above, the unobvious results obtained for this invention as seen in FIG. 8. In FIG. 8, device 10 prepared according ot the invention, is seen receiving the same pressures resulting from the sequential changes, yet retaining a desirable position in the uterus. Device 10 of FIG. 8 unexpectedly keeps its shape and position essentially free of displacement and involuntary expulsion because means 15 in cooperation with device 10 maintains the integrity of device 10 during the prolonged uterine life time.

It will be understood that those versed in the art in the light of the present specification, drawings and accompanying claims that the invention makes available to the art both a novel and useful intrauterine contraceptive device endowed with uterine retention properties that prevail during relaxed, resting pressure and contraction, while simultaneously overcoming the disadvantages associated with the prior art. It will be further understood by whose versed in the art that many different embodiments of this invention can be made without departing from the scope of the invention. Accordingly, it is to be understood the invention isnot to be construed as limited, but it embraces all equivalents inherent therein.

I claim:

1. An improved intrauterine device adapted, sized and shaped for easy insertion and use in a uterine cavity, said device having a configuration consisting of a dependent member having a lead end and a trailing end and united at the lead end to a transverse member, a sole transverse member outwardly projected from the dependent member, a left and right arm formed by the transverse member where it unites with the dependent member, the arms having an upper surface the lead end and a lower surface facing the trailing end and terminated in distant rounded ends, the improvement consisting of a restraining member at the lead end with the member raised above the surface of the transverse member to form a space between the restraining member and the transverse member, said restraining member extended towards the ends of the transverse member for preventing the arms from folding up and away from the dependent member, thereby substantially maintaining the shaped configuration of the device for a prolonged period of time when the device is placed in a viable uterine cavity.

2. The intrauterine device according to claim 1 wherein the restraining member is curved and continuous with the upper surface of the transverse member and has an internal diameter larger than the internal diameter of the dependent member.

3. The improved device according to claim 1 wherein the improvement additionally enhances insertion of the device.

4. The improved device according to claim 1 wherein the transverse member has a curved-linear convex shape and defines a pair of curved-linear arms formed where the curved-linear member is divided by the dependent member and the improvement maintains the curved-linear shape for a prolonged period of time.

5. The improved device accordint to claim 1 wherein the transverse member is wedged-shaped and angled downward from the dependent member, the improvement maintaining the angle for a prolonged period of time.

6. The improved device according to claim 1 wherein the lower surfaces of the arms are indented where the transverse member is united to the dependent member.

7. An improved intrauterine device adapted, sized and shaped for easy insertion, and use in an intrauterine cavity, said device having a configuration consisting of a dependent member having a lead end and a trailing end and united at its lead end to a transverse member, a single transverse member outwardly projected from the dependent member and consisting of left and right arms having an upper surface facing the lead end and a lower surface facing the trailing end with the arms formed where the transverse member is united to the dependent member, the improvement consisting of unidirectional means on the lower surface of the left and right arms where said arms extend from the dependent member for unidirectional downward folding of the arms to substantially prevent the arms from folding up from the independent member while simultaneously letting the arms fold downward to increase ease of insertion into the uterine cavity.

* * * * *